(12) United States Patent
Hyde et al.

(10) Patent No.: US 8,317,912 B2
(45) Date of Patent: Nov. 27, 2012

(54) WET STATE PRESERVATION OF MINERAL SLURRIES

(75) Inventors: Helen Margaret Hyde, Rochdale (GB); Fitzgerald Clarke, Gr Manchester (GB); Helmut Peters, Florstadt (DE); Terri Williams, Peyia (CY)

(73) Assignee: Arch Chemicals, Inc., Atlanta, GA (US)

( * ) Notice: Subject to any disclaimer, the term of this patent is extended or adjusted under 35 U.S.C. 154(b) by 0 days.

(21) Appl. No.: 13/415,892

(22) Filed: Mar. 9, 2012

(65) Prior Publication Data

US 2012/0247364 A1   Oct. 4, 2012

Related U.S. Application Data

(60) Provisional application No. 61/468,127, filed on Mar. 28, 2011.

(51) Int. Cl.
| | |
|---|---|
| A01N 59/02 | (2006.01) |
| A01N 59/16 | (2006.01) |
| A01N 33/00 | (2006.01) |
| A01N 43/72 | (2006.01) |
| A01N 55/02 | (2006.01) |
| C04B 103/67 | (2006.01) |

(52) U.S. Cl. ............... 106/18.33; 106/15.05; 106/18.36; 106/448; 106/465; 106/487; 424/641; 514/184; 514/186; 514/188; 514/345; 514/494; 514/500

(58) Field of Classification Search ............ 106/15.05, 106/18.33, 18.36, 448, 465, 487; 424/641; 514/184, 186, 188, 345, 360, 494, 500

See application file for complete search history.

(56) References Cited

U.S. PATENT DOCUMENTS

| | | | |
|---|---|---|---|
| 4,031,055 A | 6/1977 | Dupont et al. | |
| 4,150,026 A | 4/1979 | Miller et al. | |
| 5,208,272 A | 5/1993 | LeSota | |
| 5,227,156 A * | 7/1993 | Wiese | 514/345 |
| 5,639,803 A * | 6/1997 | Anderson et al. | 523/122 |
| 5,929,132 A * | 7/1999 | Hani et al. | 523/122 |
| 7,468,384 B2 * | 12/2008 | Levy et al. | 514/373 |
| 2004/0198713 A1 * | 10/2004 | Heer et al. | 514/184 |
| 2005/0101487 A1 * | 5/2005 | Beilfuss et al. | 504/134 |
| 2006/0035097 A1 * | 2/2006 | Batdorf | 428/507 |
| 2007/0078118 A1 * | 4/2007 | Levy et al. | 514/184 |
| 2007/0275094 A1 | 11/2007 | Thompson et al. | |
| 2007/0275945 A1 | 11/2007 | Lindner | |
| 2008/0249136 A1 * | 10/2008 | Annis et al. | 514/345 |
| 2008/0269337 A1 | 10/2008 | Breen et al. | |
| 2009/0120327 A1 | 5/2009 | Buri | |
| 2009/0325965 A1 * | 12/2009 | Annis et al. | 514/244 |

FOREIGN PATENT DOCUMENTS

| | | |
|---|---|---|
| EP | 0 741 109 A2 | 11/1996 |
| GB | 2230190 A | 10/1990 |
| JP | 57156405 A | 9/1982 |
| WO | 95/00019 | 1/1995 |
| WO | 98/31638 | 7/1998 |
| WO | 00/38520 | 7/2000 |
| WO | 2007/139645 A2 | 12/2007 |
| WO | WO2011/147558 A1 * | 12/2011 |

OTHER PUBLICATIONS

Simpson et al., Long Term Protection With Fungicide and Algicide Development, PPCJ (1996).
Mattei et al., Formulating Stable Latex Paints With Zinc Oxide, Presented at the 68th Annual Meeting of the Federation of Societies for Coating Technology in Washington, DC (1991).
"Moisturing Anti-Dandruff Shampoo," Database GNPD Mintel (2011) XP002681629, Database Accession No. 1469756.
International Search Report, dated Aug. 27, 2012, and Written Opinion, issued in corresponding PCT Application No. PCT/EP2012/055368.

* cited by examiner

*Primary Examiner* — Anthony J Green

(74) *Attorney, Agent, or Firm* — Gianna Julian-Arnold; Saul Ewing LLP

(57) ABSTRACT

The present invention relates to an antimicrobial composition comprising an isothiazolin-3-one, such as 1,2-benzisothiazolin-3-one, a zinc compound selected from zinc salts, zinc oxide, zinc hydroxide or combinations thereof, a pyrithione salt or pyrithione acid, and a surfactant selected from the group consisting of (i) an anionic surfactant having a sulfate or sulfonate moiety attached to a straight or branched chain containing from about 10 to about 18 atoms at the backbone of the chain, (ii) an anionic surfactant being an alkylaryl sulfonic acid or salt thereof wherein the alkyl portion contains from about 10 to about 18 carbon atoms, and the aryl portion contains a benzyl or substituted benzyl group, and combinations thereof. This composition is particularly effective in preventing the growth of various microorganisms in mineral slurries such as aqueous calcium carbonate slurries.

20 Claims, No Drawings

WET STATE PRESERVATION OF MINERAL SLURRIES

CROSS REFERENCE TO RELATED APPLICATIONS

This application claims priority to U.S. Provisional Application No. 61/468,127 filed Mar. 28, 2011, which is incorporated herein by reference in its entirety.

BACKGROUND OF THE INVENTION

Control of microbial growth in mineral slurries is a major concern for industrial manufacturers. Conventionally, mineral slurries are conserved using biocides. Among the widely used biocidal formulations, some contain isothiazolinones, such as 1,2-benzisothiazolin-3-one (also referred to as "BIT"). However, as noted in Patent Application Publication No. 2009/0120327, although such formulations are effective against many bacteria, they nevertheless have a lesser effectiveness against certain bacterial species. Accordingly, to compensate for this lack of efficacy against certain microbes, a large amount of BIT is typically needed to obtain reasonable performance.

For economic, environmental and toxicological considerations, it is desirable to improve the antimicrobial efficacy at a specific use level and/or reduce the amount of the biocide required for satisfactory performance in industrial applications. US Patent Application Publication No. 2007/0275094 discloses that the use of a zinc compound selected from the group consisting of zinc salts, zinc oxides, zinc hydroxides, and combinations, can improve the antimicrobial efficacy of an isothiazolin-3-one-containing composition, such as a BIT-containing one, as compared to a composition that does not contain the zinc compound. Despite of the improvements attributed to the compositions disclosed in the '094 publication, there is still a need in the biocides manufacturing community for an antimicrobial composition that is effective for use in wet state preservation of mineral slurries.

The present invention provides one such alternative.

SUMMARY OF THE INVENTION

In one aspect, the present invention relates to an antimicrobial composition comprising (a) from about 15 ppm to about 50 ppm of at least one isothiazolin-3-one, (b) from about 15 ppm to about 50 ppm of a pyrithione salt or pyrithione acid, (c) from about 35 ppm to about 135 ppm of at least one zinc compound selected from the group consisting of zinc salts, zinc oxide, zinc hydroxide, and combinations thereof, and (d) a surfactant selected from the group consisting of (i) an anionic surfactant having a sulfate or sulfonate moiety attached to a straight or branched chain containing from about 10 to about 18 atoms at the backbone of the chain, (ii) an anionic surfactant being an alkylaryl sulfonic acid or salt thereof wherein the alkyl portion contains from about 10 to about 18 carbon atoms, and the aryl portion contains a benzyl or substituted benzyl group, and combinations thereof.

In another aspect, the present invention relates to an antimicrobial composition concentrate that, upon dilution with water, provides antimicrobial efficacy. The concentrate comprises (a) from about 0.1 wt % to about 5 wt %, preferably from about 0.5 wt % to about 2 wt % of at least one isothiazolin-3-one; (b) from about 0.1 wt % to about 5 wt %, preferably from about 0.5 wt % to about 2 wt % of a pyrithione salt or pyrithione acid; (c) from about 0.5 wt % to about 10 wt %, preferably from about 1 wt % to about 5 wt % of at least one zinc compound selected from the group consisting of zinc salts, zinc oxide, zinc hydroxide, and combinations thereof; and (d) from about 5 wt % to about 20 wt %, preferably from about 10 wt % to about 15 wt % of an anionic surfactant as defined above.

In yet another aspect, the present invention relates to a mineral slurry containing the antimicrobial composition as described above, water, and an inorganic mineral selected from the group consisting of calcium carbonate, clay, titanium dioxide, and combinations thereof.

In still another aspect, the present invention relates to a method of preserving a mineral slurry containing an inorganic mineral selected from the group consisting of calcium carbonate, clay, titanium dioxide, and combinations thereof. The method comprises contacting the mineral slurry with the above described antimicrobial composition.

These and other aspects will become apparent upon reading the following detailed description of the invention.

DETAILED DESCRIPTION OF THE INVENTION

It has now been surprisingly found that an antimicrobial composition containing an isothiazolin-3-one, a zinc compound selected from the group consisting of zinc salts, zinc oxide, zinc hydroxide, and combinations thereof, a pyrithione salt or pyrithione acid, and an anionic surfactant as specified above, exhibits enhanced antimicrobial efficacy, as compared to isothiazolin-3-one-containing compositions that do not contain the surfactant. This enhanced efficacy permits achieving the desired antimicrobial activity at a lower isothiazolin-3-one usage level, or higher antimicrobial activity at a given use level, as compared to that achieved using the isothiazolin-3-one-containing composition in the absence of the surfactant.

The isothiazolin-3-one useful in the present invention is preferably an isothiazolin-3-one that is selected from: 1,2-benzisothiazolin-3-one ("BIT"), N-(n-butyl)-1,2-benzisothiazolin-3-one ("BBIT"), n-octyl-isothiazolin-one ("OIT"), 4,5-dichloro-2-n-octyl-4-isothiazolin-3-one ("DCOIT"), 2-methyl-4-isothiazolin-3-one ("MIT"), mixtures of 5-chloro-2-methyl-4-isothiazolin-3-one ("ClMIT") plus MIT (available from Rohm and Haas Company, Philadelphia, Pa. under the tradename Kathon®), dithio-2,2'-bis(benzmethylamide), and combinations thereof. Particularly preferred isothiazolin-3-ones are BIT, BBIT, and combinations thereof. In one embodiment, the preferred isothiazolin-3-one is BIT.

Suitable zinc compound is selected from the group consisting of zinc salts of organic acids, zinc salts of inorganic acids, zinc oxides, zinc hydroxides, and combinations thereof. Illustrative zinc salts include zinc chloride, zinc sulfide, zinc sulfate, zinc carbonate, basic zinc carbonate (also known as "hydroxy-containing zinc carbonate", or "zinc hydroxy carbonate" which is further identified by the empirical formula $Zn_5(OH)_6(CO_3)_2$), and combinations thereof. The zinc compound provides a source of metal ion in the antimicrobial composition. In one embodiment, the zinc compound suitable for use in the composition of the invention is zinc oxide.

Useful pyrithione salts include copper pyrithione, zinc pyrithione, sodium pyrithione. Preferably, the pyrithione salt is zinc pyrithione.

Suitable surfactant for the composition of the invention includes (i) an anionic surfactant having a sulfate or sulfonate moiety attached to a straight or branched chain containing from about 10 to about 18 atoms at the backbone of the chain, and (ii) an anionic surfactant being an alkylaryl sulfonic acid or salt thereof wherein the alkyl portion contains from about 10 to about 18 carbon atoms, and the aryl portion contains a benzyl or substituted benzyl group.

Suitable anionic surfactants having a sulfate moiety include sulfates represented by the formula $RSO_4M$, wherein R is a chain containing from about 10 to about 18 atoms at the backbone of the chain, M is a cation such as ammonium; alkanolamines, such as triethanolamine; monovalent metals, such as sodium and potassium; and polyvalent metals, such as magnesium, and calcium. In one embodiment, the anionic surfactants having a sulfate moiety are alkyl sulfates wherein R is an alkyl having from 10 to 18 carbon atoms, preferably from 10 to 16 carbon atoms, more preferably from 10 to 14 carbon atoms. R can be a straight or branched chain. Advantageously, R is a straight chain. In one embodiment, R is an octyl group.

Exemplary alkyl sulfates include sodium dodecyl sulfate, potassium dodecyl sulfate, triethylamine dodecyl sulfate, triethanolamine dodecyl sulfate, monoethanolamine dodecyl sulfate, diethanolamine dodecyl sulfate and ammonium dodecyl sulfate.

Suitable anionic surfactants having a sulfonate moiety include sulfonates having the formula $RSO_3M$, wherein R is a straight or branch chain containing 10 to 18 atoms at the backbone of the chain, M is a cation such as ammonium; alkanolamines, such as triethanolamine; monovalent metals, such as sodium and potassium; and polyvalent metals, such as magnesium, and calcium. In one embodiment, R contains a succinate group at the backbone. In another embodiment, R is an alkyl group containing from about 10 to about 18 carbon atoms, preferably from about 10 to about 16 carbon atoms, more preferably, from about 10 to about 14 carbon atoms.

Exemplary sulfonates suitable for the composition of the invention includes sodium dioctyl sulphosuccinate, and primary and secondary alkyl sulphonates.

Suitable anionic surfactant (ii) is an alkylaryl sulfonic acid or salt thereof wherein the alkyl portion contains from about 10 to about 18 carbon atoms, and the aryl portion contains a benzyl or substituted benzyl group. In one embodiment, the alkylaryl sulfonic acid is represented by the formula

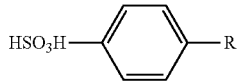

wherein R is an alkyl having from about 10 to about 18, preferably from 10 to 16, more preferably from 10 to 14 carbon atoms. In one embodiment, R is a C12 alkyl group.

In the composition, the isothiazolin-3-one is present in an amount of from about 15 to about 50 ppm, more preferably from about 20 to about 45 ppm, the zinc compound is present in an amount of from about 35 to about 135 ppm, more preferably from about 45 to about 130 ppm, the pyrithione salt of pyrithione acid is present in an amount of from about 15 to about 50 ppm, more preferably from about 20 to about 45 ppm, and the anionic surfactant is present in an amount of from about 100 ppm to about 1800 ppm, preferably from about 180 to about 1800 ppm, more preferably from about 300 to about 850 ppm, all percents are weight percents based on the total weight of the composition.

The antimicrobial composition of the invention can be provided in a ready to use form as discussed above, or alternatively, as an antimicrobial composition concentrate that, upon dilution with water, provides a working composition exhibiting desired antimicrobial efficacy. The concentrate comprises (a) at least one isothiazolin-3-one; (b) a pyrithione salt or pyrithione acid; (c) at least one zinc compound selected from the group consisting of zinc salts, zinc oxide, zinc hydroxide, and combinations thereof; and (d) an anionic surfactant as defined above. In the concentrate, component (a) is present in an amount of from about 0.1 to about 5 wt %, preferably from about 0.5 to about 2 wt %, and component (b) is present in an amount of from about 0.1 to about 5 wt %, preferably from about 0.5 to about 2 wt %, component (c) is present in an amount of from about 0.5 to about 10 wt %, preferably from about 1 to about 5 wt %, and component (d) is present in an amount of from about 5 to about 20 wt %, preferably from about 10 to about 15 wt %, wherein all percentages are based on the total weight of the concentrate.

The antimicrobial compositions of the present invention may find utility in a variety of compositions in which biocides are commonly used including, but not limited to polymer latex, paints, coatings, adhesives, functional fluids, and aqueous systems having suitable conditions conductive to the growth of microorganisms.

Advantageously, the antimicrobial compositions of the present invention are suitably used to preserve mineral slurries. Exemplary mineral slurries include, but are not limited to, aqueous dispersion of calcium carbonate, clay, and titanium dioxide. These mineral slurries can be used in the manufacturing of papers, pigments, fillers, etc.

Accordingly, in one embodiment, the invention is directed to a method of preserving mineral slurries. The method includes contacting a mineral slurry with the ready-to-use antimicrobial composition of the invention. Alternatively, the method includes diluting the antimicrobial concentrate of the invention to a ready-to-use formulation, and then contacting the ready-to-use formulation with the mineral slurry.

The present invention is also directed to mineral slurries treated with antimicrobial composition of the invention. The mineral slurry contains water, a mineral such as calcium carbonate, clay, and titanium dioxide, and the combinations thereof, and an antimicrobial composition of the invention. In one embodiment, the mineral slurry contains (a) water, (b) a mineral selected from the group consisting of calcium carbonate, clay, titanium dioxide, and combinations thereof, (c) an isothiazolin-3-one, (d) a pyrithione salt or pyrithione acid, (e) a zinc compound selected from the group consisting of zinc salts, zinc oxide, zinc hydroxide, and combinations thereof, and (f) a surfactant selected from the group consisting of (i) an anionic surfactant having a sulfate or sulfonate moiety attached to a straight or branched chain containing from about 10 to about 18 atoms at the backbone of the chain, (ii) an anionic surfactant being an alkylaryl sulfonic acid or salt thereof wherein the alkyl portion contains from about 10 to about 18 carbon atoms, and the aryl portion contains a benzyl or substituted benzyl group and combinations thereof. Preferably, the mineral is calcium carbonate. The mineral slurry may contain dispersants and other optional ingredients.

The invention is further described in the Examples given below. All percentages given herein are weight percents based on the total weight of the composition, unless otherwise stated. All patents and publications referred to in this application are incorporated herein by reference in their entireties.

Example 1

In this example, a calcium carbonate-containing aqueous slurry was sterilized to eradicate bacterial contamination by weighing out 40 g aliquots into 60 g glass bottles and autoclaving the aliquots for 20 minutes at 120° C. A series of samples were prepared by taking the 40 g aliquots of the sterilized slurry and dosing with 0.136, 0.091, 0.046, 0.023, 0.011, and 0% of a biocide composition ("Biocide A") shown in Table 1 plus 0, 0.01, 0.025, 0.05, and 0.1% of a surfactant as shown in Table 2. All samples were allowed to stand for 24 hours to equilibrate.

TABLE 1

| Biocide A (%) | BIT (ppm) | Zinc Pyrithione (ppm) | Zinc Oxide (ppm) |
|---|---|---|---|
| 0.136 | 77 | 77 | 210 |
| 0.091 | 50 | 50 | 136 |
| 0.046 | 25 | 25 | 68 |
| 0.023 | 12.5 | 12.5 | 34 |
| 0.011 | 6.25 | 6.25 | 17 |
| 0.00 | 0 | 0 | 0 |

TABLE 2

| Product Name | Description |
|---|---|
| SDS | Sodium dodecyl sulfate |
| Lutensol ® [1] | Ethoxylates of alkyl polyethylene glycol ethers |
| Ultrazine ™ NA [2] | Sodium lignosulphonate |
| Lakeland AMA LF70 ™ [3] | Di-propionate sodium salt having a structure of |

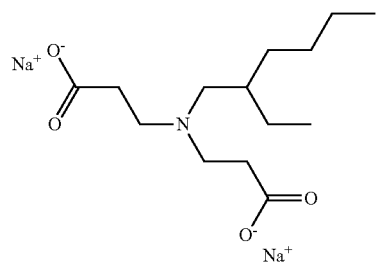

TABLE 2-continued

| Product Name | Description |
|---|---|
| Dodecyl benzene sulfonic acid | Dodecyl benzene sulfonic acid |
| Aerosol ® OT [4] | Sodium dioctyl suphosuccinate |
| Leuna alkon sulfonat 40 ™ [5] | Primary or secondary alkyl sulfonate |

[1] Available from BASF PLC.
[2] Available from Borregaard LignoTech.
[3] Available from Lakeland Laboratories Limited.
[4] Available from Cytec Industries.
[5] Available from Leuna Polymer BmBH.

After equilibration, each test sample was inoculated with 0.8 g of a contaminated slurry, the bacteria count of which is shown in Table 3. The samples were incubated at 30° C. After a contact time of 6 hours, 1, 2, 3, or 4 days, a small aliquot of each sample was streaked across the surface of nutrient agar, incubated at 30° C. for 48 hours and the surface was examined for viable colonies. The inoculation and assessment procedures were repeated at 3 or 4 day intervals for a period of 3 inoculations. The results are shown in Tables 4-8.

TABLE 3

| Week | Inoculum strength (cfu/ml) | Estimated Counts in samples (extrapolated from inoculum count) |
|---|---|---|
| 1 | 1.8E+07 | 3.6E+05 |
| 2 | 2.2E+07 | 4.4E+05 |
| 3 | 1.5E+07 | 3.0E+05 |

TABLE 4

0.136% Biocide A (Comparative)

| Biocide A (%) | surfactant | (%) | 1st inoculation (days) | | | | 2nd inoculation (days) | | | 3rd inoculation (days) | | | |
|---|---|---|---|---|---|---|---|---|---|---|---|---|---|
| | | | 0.2 | 1 | 2 | 3 | 0.2 | 1 | 4 | 0.2 | 1 | 2 | 3 |
| 0.136 | none | 0 | − | − | − | − | ++ | + | − | ++ | +/++ | − | − |
| | SDS | 0.1 | − | − | − | − | − | − | − | − | − | − | − |
| | | 0.05 | − | − | − | − | − | − | − | − | − | − | − |
| | | 0.025 | −/+ | − | − | − | − | − | − | − | − | − | − |
| | | 0.01 | − | − | − | − | + | − | − | − | − | − | − |
| | Lutensol ® | 0.1 | − | − | − | − | ++ | + | − | +/++ | − | − | − |
| | | 0.05 | <10 | − | − | − | ++ | + | − | + | − | − | − |
| | | 0.025 | − | − | − | − | ++ | − | − | +/++ | − | − | − |
| | | 0.01 | − | − | − | − | ++ | + | − | + | <10 | − | − |
| | Ultrazine ™ NA | 0.1 | + | <10 | − | <10 | ++ | + | − | ++ | <10 | − | − |
| | | 0.05 | + | <10 | − | <10 | ++ | + | − | +/++ | + | − | − |
| | | 0.025 | + | <10 | − | <10 | ++ | + | − | +/++ | + | − | − |
| | | 0.01 | + | <10 | − | <10 | ++ | + | − | ++ | + | − | − |
| | Lakeland AMA LF70 ™ | 0.1 | + | <10 | − | <10 | ++ | + | − | ++ | + | − | − |
| | | 0.05 | + | <10 | − | <10 | ++ | ++ | − | ++ | <10 | − | − |
| | | 0.025 | + | − | − | − | ++ | +++ | − | ++ | <10 | − | − |
| | | 0.01 | ++ | + | − | <10 | ++ | ++ | − | ++ | + | − | − |
| | Dodecyl benzene sulfonic acid | 0.1 | + | − | − | − | ++ | + | − | ++ | − | − | − |
| | | 0.05 | + | − | − | − | ++ | + | − | ++ | <10 | − | − |
| | | 0.025 | −/+ | − | − | − | ++ | + | − | ++ | <10 | − | − |
| | | 0.01 | + | − | − | − | ++ | + | − | ++ | <10 | − | − |
| | Aerosol ® OT | 0.1 | + | + | − | − | ++ | ++ | − | ++ | + | − | − |
| | | 0.05 | + | + | − | − | ++ | ++ | − | ++ | + | − | − |
| | | 0.025 | + | <10 | − | − | ++ | ++ | − | ++ | + | − | − |
| | | 0.01 | − | − | − | − | ++ | + | − | ++ | − | − | − |

TABLE 4-continued

0.136% Biocide A (Comparative)

| Biocide A (%) | surfactant | (%) | 1st inoculation (days) 0.2 | 1 | 2 | 3 | 2nd inoculation (days) 0.2 | 1 | 4 | 3rd inoculation (days) 0.2 | 1 | 2 | 3 |
|---|---|---|---|---|---|---|---|---|---|---|---|---|---|
| | Leuna | 0.1 | − | − | − | − | ++ | <10 | − | + | − | − | − |
| | alkon | 0.05 | − | − | − | − | ++ | <10 | − | + | − | − | − |
| | sulfonat | 0.025 | − | − | − | − | ++ | <10 | − | + | <10 | − | − |
| | 40 ™ | 0.01 | − | − | − | − | ++ | <10 | − | + | <10 | − | − |

TABLE 5

0.091% Biocide (Comparative)

| Biocide A (%) | surfactant | (%) | 1st inoculation (days) 0.2 | 1 | 2 | 3 | 2nd inoculation (days) 0.2 | 1 | 4 | 3rd inoculation (days) 0.2 | 1 | 2 | 3 |
|---|---|---|---|---|---|---|---|---|---|---|---|---|---|
| 0.091 | None | 0 | + | + | − | <10 | +++ | +++ | − | ++ | +/++ | − | − |
| | SDS | 0.1 | − | − | − | − | ++ | − | − | − | − | − | − |
| | | 0.05 | − | − | − | − | ++ | − | − | − | − | − | − |
| | | 0.025 | − | − | − | − | − | − | − | <10 | − | − | − |
| | | 0.01 | − | − | − | − | +++ | + | − | + | − | − | − |
| | Lutensol ® | 0.1 | + | <10 | − | − | <10 | + | − | ++ | + | − | − |
| | | 0.05 | + | <10 | − | − | +++ | + | − | ++ | +/++ | − | − |
| | | 0.025 | + | <10 | − | − | +++ | ++ | − | ++ | + | − | − |
| | | 0.01 | <10 | − | − | − | ++ | ++ | − | ++ | + | − | − |
| | Ultrazine ™ NA | 0.1 | + | <10 | − | <10 | ++ | + | − | ++ | +/++ | − | − |
| | | 0.05 | + | + | − | <10 | ++ | ++ | − | ++ | + | <10 | − |
| | | 0.025 | + | <10 | − | <10 | ++ | ++ | − | ++ | + | <10 | − |
| | | 0.01 | + | <10 | − | <10 | ++ | ++ | − | ++ | + | − | − |
| | Lakeland AMA LF70 ™ | 0.1 | + | − | − | <10 | ++ | ++ | − | ++ | + | <10 | − |
| | | 0.05 | + | <10 | − | <10 | ++ | ++ | − | ++ | + | <10 | − |
| | | 0.025 | + | + | − | <10 | ++ | ++ | − | ++ | +/++ | − | − |
| | | 0.01 | <10 | + | − | + | +++ | ++ | − | ++ | + | <10 | − |
| | Dodecyl benzene sulfonic acid | 0.1 | + | − | − | − | ++ | + | − | + | <10 | − | − |
| | | 0.05 | <10 | − | − | − | ++ | + | − | ++ | + | − | − |
| | | 0.025 | + | − | − | − | ++ | ++ | − | ++ | + | − | − |
| | | 0.01 | <10 | − | − | − | ++ | ++ | − | +/++ | <10 | − | − |
| | Aerosol ® OT | 0.1 | + | − | − | − | ++ | ++ | − | + | +/++ | − | − |
| | | 0.05 | +/++ | <10 | − | − | ++ | ++ | − | ++ | + | − | − |
| | | 0.025 | + | − | − | − | ++ | ++ | − | ++ | + | − | − |
| | | 0.01 | + | <10 | − | − | ++ | + | − | ++ | + | − | − |
| | Leuna alkon sulfonat 40 ™ | 0.1 | <10 | − | − | − | ++ | + | − | ++ | <10 | − | − |
| | | 0.05 | <10 | <10 | − | − | ++ | + | − | ++ | <10 | − | − |
| | | 0.025 | <10 | − | − | − | ++ | + | − | ++ | + | − | − |
| | | 0.01 | + | − | − | − | ++ | + | − | ++ | + | − | − |

TABLE 6

0.046% Biocide A

| Biocide A (%) | surfactant | (%) | 1st inoculation (days) 0.2 | 1 | 2 | 3 | 2nd inoculation (days) 0.2 | 1 | 4 | 3rd inoculation (days) 0.2 | 1 | 2 | 3 |
|---|---|---|---|---|---|---|---|---|---|---|---|---|---|
| 0.046 | None | 0 | ++ | ++ | <10 | + | +++ | ++ | ++ | +++ | +++ | +++ | +++ |
| | SDS | 0.1 | <10 | − | − | − | ++ | <10 | − | +++ | + | − | − |
| | | 0.05 | <10 | − | − | − | ++ | <10 | − | +++ | + | − | − |
| | | 0.025 | + | − | − | − | +++ | + | − | +++ | + | − | − |
| | | 0.01 | ++ | <10 | − | − | +++ | ++ | − | +++ | ++ | + | <10 |
| | Lutensol ® (Comparative) | 0.1 | ++ | ++ | − | − | +++ | ++ | <10 | +++ | ++ | +++ | + |
| | | 0.05 | ++ | ++ | − | − | +++ | ++ | − | +++ | ++ | ++ | + |
| | | 0.025 | ++ | ++ | − | − | +++ | ++ | <10 | +++ | ++ | +++ | ++ |
| | | 0.01 | +++ | ++ | − | − | +++ | ++ | + | +++ | ++ | ++ | ++ |
| | Ultrazine ™ NA (Comparative) | 0.1 | +++ | ++ | <10 | +/++ | +++ | ++ | +++ | +++ | +++ | +++ | +++ |
| | | 0.05 | +++ | ++ | − | + | +++ | ++ | +++ | +++ | +++ | +++ | +++ |
| | | 0.025 | ++ | ++ | <10 | + | +++ | ++ | +++ | +++ | +++ | +++ | +++ |
| | | 0.01 | ++ | ++ | <10 | + | +++ | ++ | +/++ | +++ | ++ | ++ | ++ |
| | Lakeland AMA | 0.1 | ++ | + | <10 | +/++ | +++ | ++ | − | +++ | ++ | + | ++ |
| | | 0.05 | ++ | + | − | +/++ | +++ | +++ | − | +++ | ++ | ++ | ++ |

TABLE 6-continued 0.046% Biocide A

| Biocide A (%) | surfactant | (%) | 1st inoculation (days) | | | | 2nd inoculation (days) | | | 3rd inoculation (days) | | | |
|---|---|---|---|---|---|---|---|---|---|---|---|---|---|
| | | | 0.2 | 1 | 2 | 3 | 0.2 | 1 | 4 | 0.2 | 1 | 2 | 3 |
| | LF70 ™ | 0.025 | ++ | ++ | − | + | +++ | ++ | − | +++ | +++ | +++ | +++ |
| | (Comparative) | 0.01 | ++ | + | <10 | +/++ | +++ | ++ | − | +++ | ++ | ++ | +++ |
| | Dodecyl | 0.1 | ++ | − | − | − | +++ | ++ | − | +++ | +/++ | <10 | − |
| | benzene | 0.05 | ++ | + | − | − | +++ | +/++ | − | +++ | ++ | <10 | − |
| | sulfonic acid | 0.025 | ++ | + | − | − | +++ | ++ | − | +++ | +/++ | <10 | − |
| | | 0.01 | ++ | + | − | − | +++ | ++ | − | +++ | ++ | − | − |
| | Aerosol ® | 0.1 | ++ | ++ | − | − | +++ | ++ | − | +++ | + | − | − |
| | OT | 0.05 | +++ | ++ | − | − | +++ | ++ | − | +++ | ++ | − | − |
| | | 0.025 | ++ | ++ | − | − | +++ | ++ | − | +++ | ++ | − | − |
| | | 0.01 | ++ | ++ | − | − | +++ | ++ | − | +++ | ++ | − | − |
| | Leuna | 0.1 | ++ | <10 | − | − | +++ | ++ | − | +++ | ++ | − | − |
| | alkon | 0.05 | ++ | + | − | − | +++ | ++ | − | +++ | ++ | − | − |
| | sulfonat | 0.025 | ++ | + | − | − | +++ | ++ | − | +++ | ++ | − | − |
| | 40 ™ | 0.01 | ++ | + | − | − | +++ | ++ | − | +++ | ++ | − | − |

TABLE 7

0.023% Biocide (Comparative)

| Biocide A (%) | surfactant | (%) | 1st inoculation (days) | | | | 2nd inoculation (days) | | | 3rd inoculation (days) | | | |
|---|---|---|---|---|---|---|---|---|---|---|---|---|---|
| | | | 0.2 | 1 | 2 | 3 | 0.2 | 1 | 4 | 0.2 | 1 | 2 | 3 |
| 0.023 | None | 0 | +++ | ++ | ++ | +++ | +++ | +++ | +++ | +++ | +++ | +++ | +++ |
| | SDS | 0.1 | ++ | − | − | − | +++ | ++ | − | +++ | +++ | +++ | +++ |
| | | 0.05 | ++ | − | − | − | +++ | ++ | ++ | +++ | +++ | +++ | +++ |
| | | 0.025 | +++ | <10 | − | − | +++ | +++ | +++ | +++ | ++ | +++ | +++ |
| | | 0.01 | +++ | + | − | <10 | +++ | +++ | +++ | +++ | +++ | +++ | +++ |
| | Lutensol ® | 0.1 | +++ | ++ | + | ++ | +++ | +++ | +++ | SAMPLES FAILED TEST COMPLETED | | | |
| | | 0.05 | +++ | ++ | + | ++ | +++ | +++ | +++ | | | | |
| | | 0.025 | +++ | ++ | +++ | +++ | +++ | +++ | +++ | | | | |
| | | 0.01 | +++ | ++ | ++ | ++ | +++ | +++ | +++ | | | | |
| | Ultrazine ™ NA | 0.1 | +++ | +++ | +++ | +++ | +++ | +++ | +++ | SAMPLES FAILED TEST COMPLETED | | | |
| | | 0.05 | +++ | ++ | + | +++ | +++ | +++ | +++ | | | | |
| | | 0.025 | +++ | ++ | + | ++ | +++ | +++ | +++ | | | | |
| | | 0.01 | +++ | ++ | + | ++ | +++ | +++ | +++ | | | | |
| | Lakeland AMA LF70 ™ | 0.1 | +++ | ++ | + | +++ | +++ | +++ | ++ | SAMPLES FAILED TEST COMPLETED | | | |
| | | 0.05 | +++ | ++ | + | +++ | +++ | +++ | +++ | | | | |
| | | 0.025 | +++ | ++ | + | ++ | +++ | +++ | +++ | | | | |
| | | 0.01 | +++ | ++ | + | +++ | +++ | +++ | +++ | | | | |
| | Dodecyl benzene sulfonic acid | 0.1 | +++ | ++ | <10 | <10 | +++ | + | +++ | SAMPLES FAILED TEST COMPLETED | | | |
| | | 0.05 | +++ | ++ | <10 | <10 | +++ | +++ | +++ | | | | |
| | | 0.025 | +++ | ++ | − | +++ | +++ | +++ | +++ | | | | |
| | | 0.01 | +++ | ++ | <10 | ++ | +++ | +++ | +++ | | | | |
| | Aerosol ® OT | 0.1 | +++ | ++ | + | ++ | +++ | +++ | +++ | SAMPLES FAILED TEST COMPLETED | | | |
| | | 0.05 | +++ | ++ | + | + | +++ | +++ | +++ | | | | |
| | | 0.025 | +++ | ++ | ++ | +++ | +++ | +++ | +++ | | | | |
| | | 0.01 | +++ | ++ | − | − | +++ | +++ | +++ | | | | |
| | Leuna alkon sulfonat 40 ™ | 0.1 | +++ | + | − | − | +++ | ++ | +++ | SAMPLES FAILED TEST COMPLETED | | | |
| | | 0.05 | +++ | ++ | − | − | +++ | +++ | +++ | | | | |
| | | 0.025 | +++ | ++ | − | − | +++ | +++ | +++ | | | | |
| | | 0.01 | +++ | ++ | − | + | +++ | +++ | +++ | | | | |

TABLE 8

Untreated with Biocide A (Comparative)

| Biocide A (%) | surfactant | (%) | 1st inoculation (days) | | | | 2nd inoculation (days) | | | 3rd inoculation (days) | | | |
|---|---|---|---|---|---|---|---|---|---|---|---|---|---|
| | | | 0.2 | 1 | 2 | 3 | 0.2 | 1 | 4 | 0.2 | 1 | 2 | 3 |
| 0 | none | 0 | +++ | +++ | +++ | +++ | +++ | +++ | +++ | +++ | +++ | +++ | +++ |
| | SDS | 0.1 | +++ | +++ | +++ | +++ | SAMPLES FAILED TEST COMPLETED | | | SAMPLES FAILED TEST COMPLETED | | | |
| | | 0.05 | +++ | +++ | +++ | +++ | | | | | | | |
| | | 0.025 | +++ | +++ | +++ | +++ | | | | | | | |
| | | 0.01 | +++ | +++ | +++ | +++ | | | | | | | |
| | Lutensol ® | 0.1 | +++ | +++ | +++ | +++ | SAMPLES FAILED TEST COMPLETED | | | SAMPLES FAILED TEST COMPLETED | | | |
| | | 0.05 | +++ | +++ | +++ | +++ | | | | | | | |
| | | 0.025 | +++ | +++ | +++ | +++ | | | | | | | |
| | | 0.01 | +++ | +++ | ++ | +++ | | | | | | | |
| | Ultrazine ™ NA | 0.1 | +++ | +++ | +++ | +++ | SAMPLES FAILED TEST COMPLETED | | | SAMPLES FAILED TEST COMPLETED | | | |
| | | 0.05 | +++ | +++ | +++ | +++ | | | | | | | |
| | | 0.025 | +++ | +++ | +++ | +++ | | | | | | | |
| | | 0.01 | +++ | +++ | +++ | +++ | | | | | | | |
| | Lakeland AMA LF70 ™ | 0.1 | +++ | +++ | +++ | +++ | SAMPLES FAILED TEST COMPLETED | | | SAMPLES FAILED TEST COMPLETED | | | |
| | | 0.05 | +++ | +++ | +++ | +++ | | | | | | | |
| | | 0.025 | +++ | +++ | +++ | +++ | | | | | | | |
| | | 0.01 | +++ | +++ | +++ | +++ | | | | | | | |
| | Dodecyl benzene sulfonic acid | 0.1 | +++ | +++ | +++ | +++ | SAMPLES FAILED TEST COMPLETED | | | SAMPLES FAILED TEST COMPLETED | | | |
| | | 0.05 | +++ | +++ | +++ | +++ | | | | | | | |
| | | 0.025 | +++ | +++ | +++ | +++ | | | | | | | |
| | | 0.01 | +++ | +++ | +++ | +++ | | | | | | | |
| | Aerosol ® OT | 0.1 | +++ | +++ | +++ | +++ | SAMPLES FAILED TEST COMPLETED | | | SAMPLES FAILED TEST COMPLETED | | | |
| | | 0.05 | +++ | +++ | +++ | +++ | | | | | | | |
| | | 0.025 | +++ | +++ | +++ | +++ | | | | | | | |
| | | 0.01 | +++ | +++ | +++ | +++ | | | | | | | |
| | Leuna alkon sulfonat 40 ™ | 0.1 | +++ | +++ | +++ | +++ | SAMPLES FAILED TEST COMPLETED | | | SAMPLES FAILED TEST COMPLETED | | | |

Key for Tables 4-8
− = no growth (no visible colonies)
<10 = very light growth
+ = light growth
++ = moderate growth
+++ = heavy growth Tables 4 and 5 indicate that an amount of biocide A of 0.136% or of 0.091% alone is sufficient to provide antimicrobial efficacy at the level of usage.

Table 6 indicates that when biocide A is used at an amount of 0.046%, the presence of surfactants improves its efficacy for preserving contaminated slurry. As a comparison, Table 7 indicates that none of the tested surfactant by itself at a dosage level of up to 0.1% shows any efficacy in preserving contaminated slurry.

Table 7 indicates that an amount of biocide A of 0.023% is inadequate to provide the desired protection to the contaminated slurry even when used together with 0.1% of tested surfactants.

The data shown in Tables 4-8 demonstrate that a composition containing between 0.03% and 0.09% of biocide A and a surfactant being SDS, dodecyl benzene sulfonic acid, Aerosol® OT and Leuna alkon sulfonat 40™ shows improved efficacy in preserving contaminated slurry as compared to biocide A and the surfactant used alone.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. An antimicrobial composition comprising (a) from about 15 ppm to about 50 ppm of at least one isothiazolin-3-one, (b) from about 15 ppm to about 50 ppm of a pyrithione salt or pyrithione acid, (c) from about 35 ppm to about 135 ppm of at least one zinc compound selected from the group consisting of zinc salts, zinc oxide, zinc hydroxide, and combinations thereof, and (d) a surfactant selected from the group consisting of (i) an anionic surfactant having a sulfate or sulfonate moiety attached to a straight or branched chain containing from about 10 to about 18 atoms at the backbone of the chain, (ii) an anionic surfactant being an alkylaryl sulfonic acid or salt thereof wherein the alkyl portion contains from about 10 to about 18 carbon atoms, and the aryl portion contains a benzyl or substituted benzyl group, and combinations thereof.

2. The antimicrobial composition of claim 1 wherein component (d) is present in an amount of from about 180 ppm to about 1800 ppm based on the total weight of the composition.

3. The antimicrobial composition of claim 1 wherein said isothiazolin-3-one is selected from the group consisting of 1,2-benzisothiazolin-3-one, N-(n-butyl)-1,2-benzisothiazolin-3-one, 4,5-dichloro-2-n-octyl-4-isothiazolin-3-one, 2-methyl-4-isothiazolin-3-one, mixtures of 5-chloro-2-methyl-4-isothiazolin-3-one (C1MIT) and 2-methyl-4-isothiazolin-3-one, and dithio-2,2'-bis(benzmethylamide), and combinations thereof.

4. The antimicrobial composition of claim 1 wherein said zinc salt is selected from the group consisting of zinc chloride, zinc sulfide, zinc sulfate, zinc carbonate, basic zinc carbonate, and combinations thereof.

5. The antimicrobial composition of claim 1 wherein said zinc compound is zinc oxide.

6. The antimicrobial composition of claim 1 wherein said pyrithione salt is selected from the group consisting of zinc pyrithione, sodium pyrithione, copper pyrithione, and combinations thereof.

7. The antimicrobial composition of claim 1 wherein said surfactant is selected from the group consisting of sodium dodecyl sulfate, dodecyl benzene sulfonic acid and salts thereof, sodium dioctyl suphosuccinate, primary or secondary alkyl sulfonates, and combinations thereof.

8. An antimicrobial composition concentrate, which upon dilution with water provides the amounts of components (a), (b), (c), and (d) as specified in claim 1, said concentrate comprising component (a) in an amount of between about 0.1 and about 5 wt %, component (b) in an amount of between about 0.1 and about 5 wt %, and component (c) in an amount of between about 0.5 and about 10 wt %, all based on the total weight of the antimicrobial composition concentrate.

9. The antimicrobial composition concentrate of claim 8 wherein component (d) is present in an amount of from about 5 to about 20 wt % based on the total weight of the antimicrobial composition concentrate.

10. A mineral slurry comprising (a) water, (b) a mineral selected from the group consisting of calcium carbonate, clay, titanium dioxide, and combinations thereof, (c) an isothiazolin-3-one, (d) a pyrithione salt or pyrithione acid, (e) a zinc compound selected from the group consisting of zinc salts, zinc oxide, zinc hydroxide, and combinations thereof, and (f) a surfactant selected from the group consisting of (i) an anionic surfactant having a sulfate or sulfonate moiety attached to a straight or branched chain containing from about 10 to about 18 atoms at the backbone of the chain, (ii) an anionic surfactant being an alkylaryl sulfonic acid or salt thereof wherein the alkyl portion contains from about 10 to about 18 carbon atoms, and the aryl portion contains a benzyl or substituted benzyl group, and combinations thereof.

11. The mineral slurry of claim 10 wherein said isothiazolin-3-one is selected from the group consisting of 1,2-benzisothiazolin-3-one, N-(n-butyl)-1,2-benzisothiazolin-3-one, 4,5-dichloro-2-n-octyl-4-isothiazolin-3-one, 2-methyl-4-isothiazolin-3-one, mixtures of 5-chloro-2-methyl-4-isothiazolin-3-one (C1MIT) and 2-methyl-4-isothiazolin-3-one, and dithio-2,2'-bis(benzmethylamide), and combinations thereof.

12. The mineral slurry of claim 10 wherein said isothiazolin-3-one is 1,2-benzisothiazolin-3-one.

13. The mineral slurry of claim 10 wherein said zinc salt is selected from the group consisting of zinc chloride, zinc sulfide, zinc sulfate, zinc carbonate, basic zinc carbonate, and combinations thereof.

14. The mineral slurry of claim 10 wherein said zinc compound is zinc oxide.

15. The mineral slurry of claim 10 wherein said pyrithione salt is selected from the group consisting of zinc pyrithione, sodium pyrithione, copper pyrithione, and combinations thereof.

16. The mineral slurry of claim 10 wherein said pyrithione salt is zinc pyrithione.

17. The mineral slurry of claim 10 wherein said surfactant is selected from the group consisting of sodium dodecyl sulfate, dodecyl benzene sulfonic acid and salts thereof, sodium dioctyl suphosuccinate, primary or secondary alkyl sulfonates, and combinations thereof.

18. The mineral slurry of claim 16 wherein said surfactant is sodium dodecyl sulfate.

19. A method to preserve a mineral slurry comprising contacting the mineral slurry with the antimicrobial composition of claim 1.

20. The method of claim 19 wherein the mineral slurry is an aqueous dispersion of a mineral selected from the group consisting of calcium carbonate, clay, titanium dioxide, and combinations thereof.

* * * * *